(12) United States Patent　　(10) Patent No.: US 9,265,333 B2
　　Huang　　　　　　　　　　　　(45) Date of Patent: Feb. 23, 2016

(54) ANTI-LOOSE INTERDENTAL BRUSH

(71) Applicant: Ya-Lin Huang, Kaohsiung (TW)

(72) Inventor: Ya-Lin Huang, Kaohsiung (TW)

(*) Notice: Subject to any disclaimer, the term of this patent is extended or adjusted under 35 U.S.C. 154(b) by 378 days.

(21) Appl. No.: 13/863,502

(22) Filed: Apr. 16, 2013

(65) Prior Publication Data

US 2014/0304933 A1　　Oct. 16, 2014

(51) Int. Cl.
　　*A46B 3/18*　　　(2006.01)
　　*A61C 15/00*　　(2006.01)

(52) U.S. Cl.
　　CPC . *A46B 3/18* (2013.01); *A61C 15/00* (2013.01); *A46B 2200/108* (2013.01)

(58) Field of Classification Search
　　CPC .. A46B 9/021; A46B 2200/1053; A46B 3/18; A46B 2200/106; A46B 5/00; A46B 9/02; A46B 9/04; A46B 9/10; A61C 15/00
　　See application file for complete search history.

(56) References Cited

U.S. PATENT DOCUMENTS 8,256,848 B2 *　9/2012　Lee ................................. 300/21
2011/0314624 A1 * 12/2011　Kubo .......................... 15/167.1

* cited by examiner

*Primary Examiner* — Robert Scruggs
(74) *Attorney, Agent, or Firm* — Alan D. Kamrath; Kamrath IP Lawfirm, P.A.

(57) ABSTRACT

An anti-loose interdental brush includes a plurality of fixing portions formed on a bristle stem of an interdental brush. Each fixing portion includes a bottom wall, a side wall formed laterally from the bottom wall, and a capacity area surrounded by the bottom wall and the side wall. The adjacent bottom walls of the adjacent fixing portions are orientated in different directions. Thus, the adjacent capacity areas are set in different directions to contact the handle. An outer diameter of the bottom wall can be preferably larger than or equal to an outer diameter of the bristle stem. Accordingly, a dual engaging and fixing effect between the bristle stem and the handle is attained to prevent the bristle stem from loosening and rotating due to an external force and to enhance safety in using.

6 Claims, 6 Drawing Sheets

ANTI-LOOSE INTERDENTAL BRUSH

BACKGROUND OF THE INVENTION

1. Field of the Invention

The present invention relates to an interdental brush, particularly to an anti-loose interdental brush.

2. Description of the Related Art

Referring to FIG. 1, the conventional interdental brush 1 mainly comprises a bristle stem 11, a plurality of bristles 12, and a handle 13. The bristle stem 11 is formed by a plurality of interlaced wires. The bristles 12 are wound and clamped by the bristle stem 11 for orientating. The handle 13 is directly formed by plastic material and covers the bristle stem 11. While using, a user holds the handle 13 and stretches the interdental brush 1 into the mouth (not shown), so that the bristles 12 start to clean the tooth slits. However, the bristle stem 11 covered by the plastic handle 13 only attains the simple engagement. Therefore, the bristle stem 11 is easily loosened, while the user moves or rotates the interdental brush 1 in using. Moreover, the disengaged bristle stem 11 is easy to be swallowed and dangerous for the user. Hence, the interdental brush 1 should be improved.

In order to solve the aforementioned lack of engaging, a Taiwan patent number M314550, entitled "An anti-loose interdental brush", discloses a bristle stem punched to form a fixing portion. Because the property of an outer diameter of the fixing portion is larger than an outer diameter of the bristle stem, the bristle stem can be firmly engaged in the handle. A Taiwan patent number I3747024 entitled "A method for making interdental brush", discloses a bristle stem punched to form a plurality of expanding portions with an outer diameter larger than a diameter of the bristle stem. Further, the outermost diameter of the expanding portions is larger than the diameter of a through hole of a handle. Although the aforementioned prior arts attain the engaging and fixing effect of the bristle stem and the handle, there is still a need to be improved after many times of practical tests.

SUMMARY OF THE INVENTION

It is therefore the purpose of this invention to provide an anti-loose interdental brush for effectively enhancing the dual engaging and fixing effect between the bristle stem and the handle in order to prevent the bristle stem from loosening or rotating due to an external force and to enhance safety in using.

The anti-loose interdental brush in accordance with the present invention comprises a bristle stem, a plurality of bristles, and a handle. A plurality of fixing portions is formed on the bristle stem. Each fixing portion includes a bottom wall, a side wall formed laterally from the bottom wall, and a capacity area surrounded by the bottom wall and the side wall. The adjacent bottom walls of the adjacent fixing portions are orientated in different directions. Thus, the adjacent capacity areas are set in different directions to provide a dual engaging and fixing effect between the bristle stem and the handle. Moreover, an outer diameter of the bottom wall can be preferably larger than or equal to an outer diameter of the bristle stem. Accordingly, a dual engaging and fixing effect of the bristle stem and the handle is attained to prevent the bristle stem from loosening and rotating due to an external force and to enhance safety in using.

Preferably, the adjacent fixing portions intersect with each other.

Preferably, an outer diameter of the bottom wall is larger than an outer diameter of the bristle stem.

Preferably, an outer diameter of the bottom wall is equal to an outer diameter of the bristle stem.

The advantages of the present invention over the known prior arts will become more apparent to those of ordinary skilled in the art by reading the following descriptions with the relating drawings.

DETAILED DESCRIPTION OF THE PREFERRED EMBODIMENTS

Figure 1:
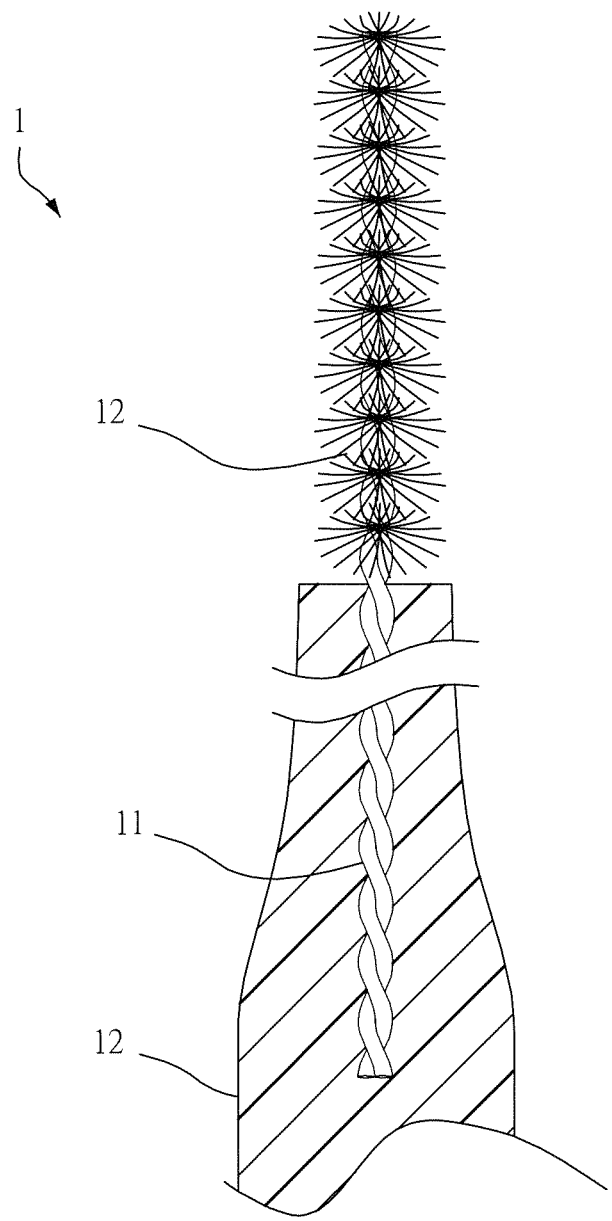
FIG. 1 is a schematic view showing a conventional interdental brush.

Wherever possible, the same reference numbers are used in the drawings and the description to refer to the same or like parts.

Figure 2:
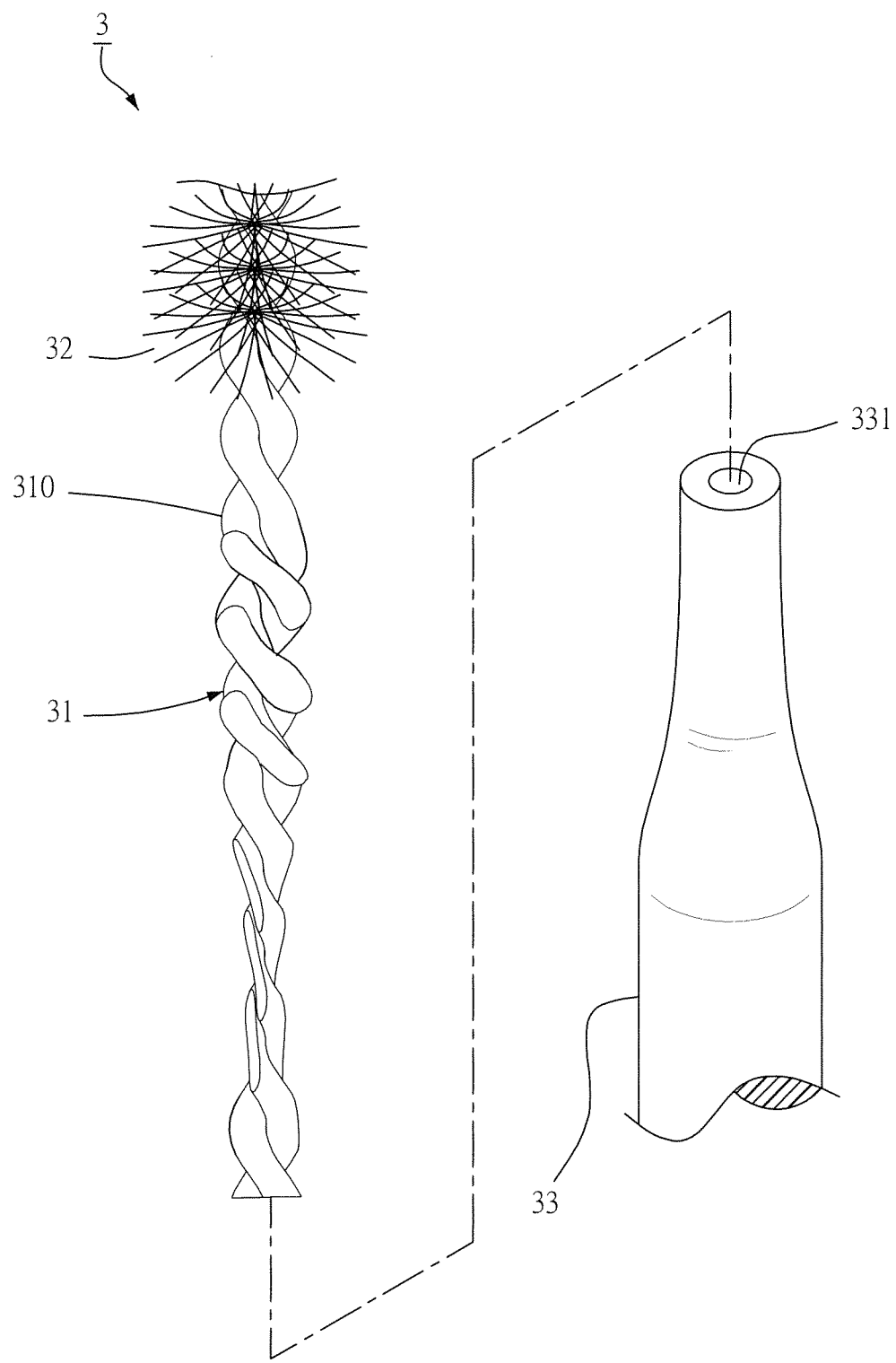
FIG. 2 is a perspective view showing a first preferred embodiment of the present invention.

Referring to FIG. 2, a first preferred embodiment of the present invention is shown. An anti-loose interdental brush 3 comprises a bristle stem 31 formed by at least one interlaced wire 310, a plurality of bristles 32 wound and clamped by the wire 310 of the bristle stem 31, and a handle 33 firmly disposed on the bristle stem 31. A through hole 331 is formed on the handle 33 for the bristle stem 31 to pass through and be fixed in the through hole 331.

Figure 3:
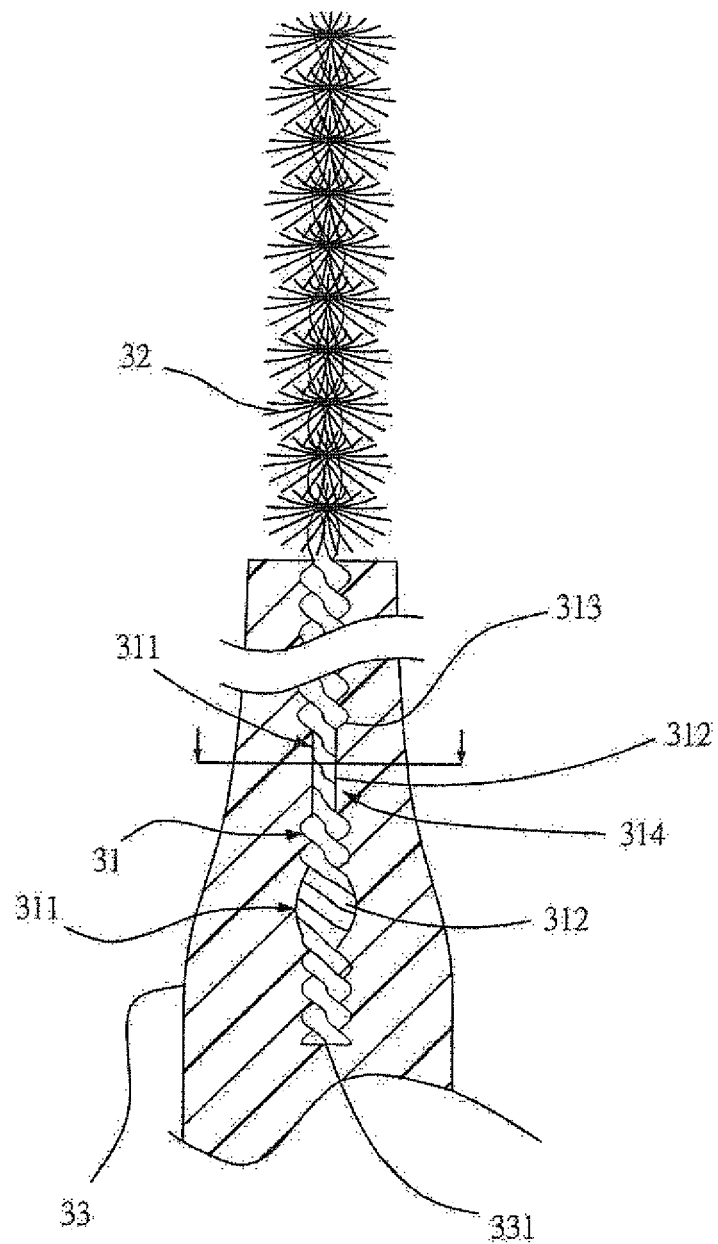
FIG. 3 is a side view of the preferred embodiment of the present invention.
Figure 4:
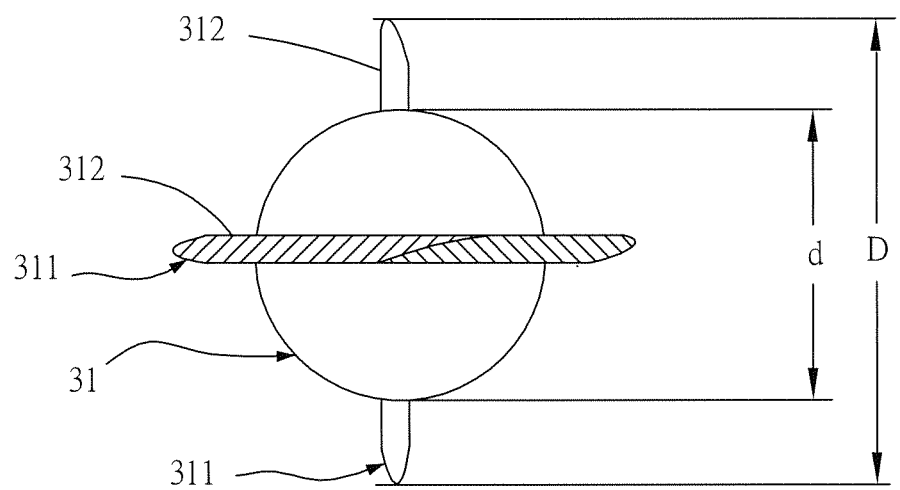
FIG. 4 is a cross-sectional view of the preferred embodiment of the present invention in FIG. 3.
Figure 5:
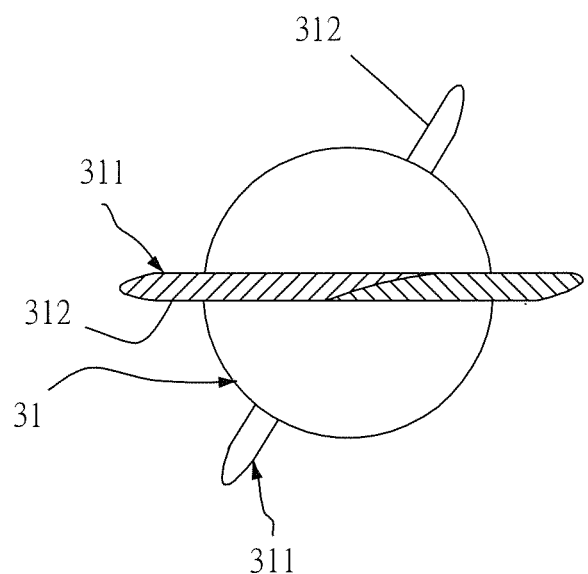
FIG. 5 is a cross-sectional view of a further preferred embodiment of the present invention.
Figure 6:
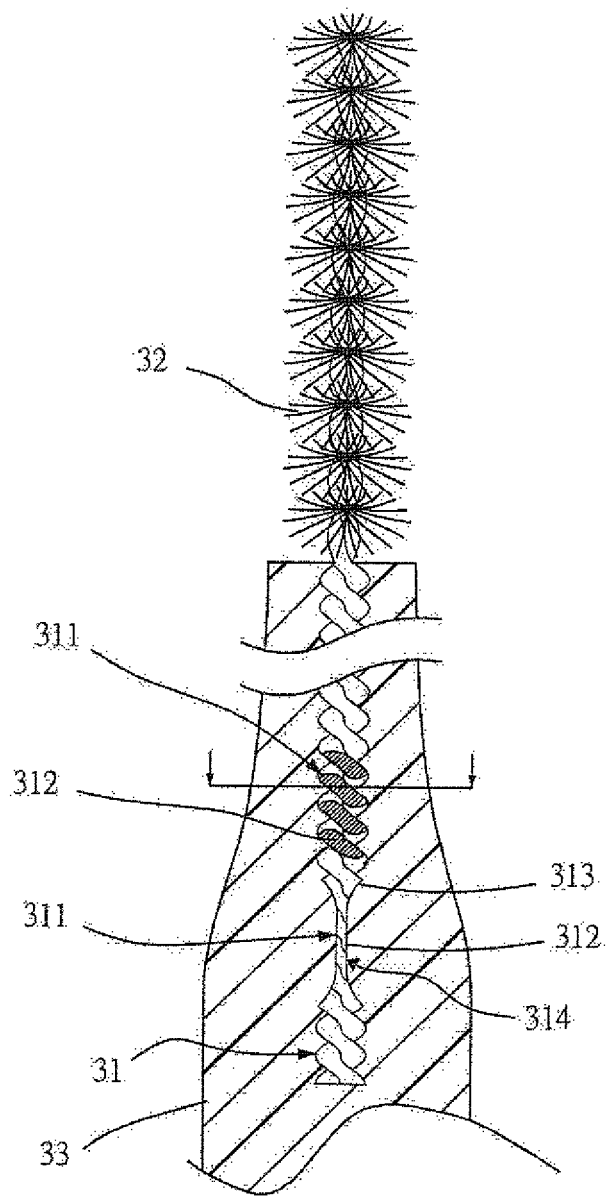
FIG. 6 is a side view of a further preferred embodiment of the present invention.
Figure 7:
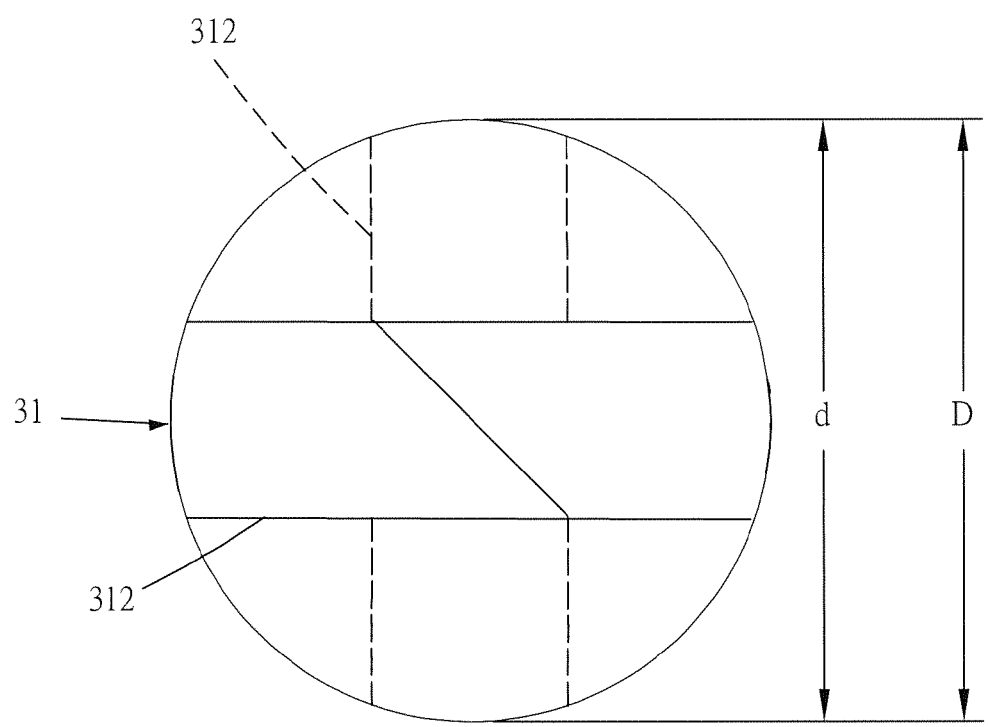
FIG. 7 is a cross-sectional view of the further preferred embodiment of the present invention in FIG. 6.

Referring to FIG. 3, in this preferred embodiment, the bristle stem 31 is formed by two interlaced wires 310. The bristles 32 are wound and clamped by the wires 310 on the bristle stem 31, so that the bristles 32 transversely project out of the bristle stem 31. A plurality of fixing portions 311 is formed on the bristle stem 31. Herein, two fixing portions 311 are described in this preferred embodiment. Each fixing portion 311 includes a bottom wall 312, a side wall 313 formed laterally from the bottom wall 312, and a capacity area 314 surrounded by the bottom wall 312 and the side wall 313. Herein, only one capacity area 314 of the fixing portion 311 is marked in FIG. 3. Furthermore, each bottom wall 312 of each fixing portion 311 is orientated in a direction different from the adjacent bottom wall 312 of the adjacent fixing portion 311. Thus, the adjacent capacity areas 314 are set in different directions to contact the handle 33. The fixing portions 311 are intersected with each other. Namely the bottom walls 312 of the adjacent fixing portions 311 are set in a perpendicular and intersected direction (as shown in FIG. 4). Furthermore, the bottom walls 312 of the fixing portions 311 can be inclined with each other and in an intersected direction with unspecified angles (as shown in FIG. 5). In the preferred embodiment of the present invention, the fixing portions 311 are described perpendicular and intersected with each other for providing a dual effect, so that the inner side of the handle 33 can be firmly fixed to the fixing portions 311 of the bristle stem 31. Moreover, the outer diameter of the bottom wall 312 can be shown in different lengths for enhancing the engaging effect between the handle 33 and the bristle stem 31. That is to say, the outer diameter D of the bottom wall 312 can be larger than the diameter d of the bristle stem 31 (as shown in FIGS. 3 and 4) or the outer diameter D of the bottom wall 312 can be equal to the diameter d of the bristle stem 31 (as shown in FIGS. 6 and 7). Herein, only FIG. 4 is described.

Referring to FIGS. 2, 3, and 4, during the manufacturing procedure of the interdental brush 3, the bristle stem 31 is formed by a punching apparatus (not shown). Namely, an appropriate place of the bristle stem 31 is punched for forming a plurality of flat fixing portions 311, so that two corresponding capacity areas 314 are formed on the bristle stem 31. Therefore, the bristle stem 31 is presented as a non-single pillar when the fixing portions 311 intersect. Because the bottom walls of the fixing portions 311 are disposed in different directions, the capacity areas 314 and the handle 33 present an engaging effect with different directions in combination. After the bristle stem 31 is inserted in the through hole 331 and covered by the handle 33, the bristle stem 31 engage and fix the intersected fixing portions 311 in the handle 33. The outer diameter D of the bottom wall 312 can be larger than the diameter d of the bristle stem 31 in order to attain a dual engaging and fixing effect between the handle 33 and the bristle stem 31. Because the intersected fixing portions 311 are disposed in different directions, a dual engaging effect is generated between the bristle stem 31 and the handle 33. Therefore, the bristle stem 31 does not loosen or rotate due to the external force even when the user exerts a force, such as straight movement or rotation to the interdental brush 3. The user does not have to worry about the bristle stem 31 being disengaged or swallowed in use, which enhances safety in using.

To sum up, the anti-loose interdental brush makes use of a plurality of fixing areas formed on the bristle stem and a plurality of bottom walls of the fixing areas disposed in different directions to provide a dual engaging and fixing effect between the bristle stem and the handle. Moreover, an outer diameter of the bottom wall can be larger than an outer diameter of the bristle stem to prevent the bristle stem from loosening and rotating due to an external force and to enhance safety in using.

While the embodiments in accordance with the present invention have been shown and described, it should be clear to those skilled in the art that further embodiments may be made without departing from the scope of the present invention.

I claim:

1. An anti-loose interdental brush comprising a bristle stem extending in a longitudinal direction and formed by at least one interlaced wire, a plurality of bristles wound and clamped by said at least one interlaced wire of said bristle stem, and a handle firmly fixed around said bristle stem;

wherein a plurality of fixing portions is formed on said bristle stem, is located inside the handle, and is spaced from each other in the longitudinal direction; with each fixing portion including a bottom wall extending tangentially to the longitudinal direction and at a radial distance less than the bristle stem, a side wall formed laterally from said bottom wall, and a capacity area surrounded by said bottom wall and said side wall; with each bottom wall of each fixing portion orientated in a radial direction from the longitudinal direction different from an adjacent bottom wall of an adjacent fixing portion, wherein adjacent capacity areas are set in different directions to contact said handle in order to firmly fix an inner side of said handle to said plurality of fixing portions.

2. The anti-loose interdental brush as claimed in claim 1, wherein said bottom walls of said adjacent fixing portions are perpendicular with each other.

3. The anti-loose interdental brush as claimed in claim 2, wherein an outer diameter of said bottom wall is larger than an outer diameter of said bristle stem.

4. The anti-loose interdental brush as claimed in claim 2, wherein an outer diameter of said bottom wall is equal to an outer diameter of said bristle stem.

5. The anti-loose interdental brush as claimed in claim 1, wherein an outer diameter of said bottom wall is larger than an outer diameter of said bristle stem.

6. The anti-loose interdental brush as claimed in claim 1, wherein an outer diameter of said bottom wall is equal to an outer diameter of said bristle stem.

\* \* \* \* \*